US011612629B2

(12) United States Patent
Jung et al.

(10) Patent No.: US 11,612,629 B2
(45) Date of Patent: Mar. 28, 2023

(54) PHARMACEUTICAL COMPOSITION FOR PREVENTING OR TREATING MUSCLE DISEASES, CONTAINING GINSENG BERRY EXTRACT AS ACTIVE INGREDIENT

(71) Applicant: Holistic Bio Co., Ltd., Seongnam-si (KR)

(72) Inventors: Woo Chang Jung, Seoul (KR); Sang Jun Lee, Seongnam-si (KR); Se Young Jung, Seoul (KR)

(73) Assignee: HOLISTIC BIO CO., LTD., Seongnam-si (KR)

( * ) Notice: Subject to any disclaimer, the term of this patent is extended or adjusted under 35 U.S.C. 154(b) by 52 days.

(21) Appl. No.: 17/269,514

(22) PCT Filed: Jul. 19, 2019

(86) PCT No.: PCT/KR2019/008925
§ 371 (c)(1),
(2) Date: Feb. 18, 2021

(87) PCT Pub. No.: WO2020/040432
PCT Pub. Date: Feb. 27, 2020

(65) Prior Publication Data
US 2021/0213085 A1 Jul. 15, 2021

(30) Foreign Application Priority Data

Aug. 20, 2018 (KR) .................. 10-2018-0096883

(51) Int. Cl.
*A61K 36/00* (2006.01)
*A61K 36/258* (2006.01)
*A61P 21/00* (2006.01)

(52) U.S. Cl.
CPC ............ *A61K 36/258* (2013.01); *A61P 21/00* (2018.01)

(58) Field of Classification Search
CPC .............................. A61P 21/00; A61K 36/258
See application file for complete search history.

(56) References Cited

FOREIGN PATENT DOCUMENTS

| KR | 10-2011-0079564 | 7/2011 | | |
|---|---|---|---|---|
| KR | 10-1241050 | 3/2013 | | |
| KR | 10-1484502 | 1/2015 | | |
| KR | 10-1581497 | 12/2015 | | |
| KR | 10-2017-0001037 | 1/2017 | | |
| KR | 20170019399 A | * | 2/2017 | |
| KR | 10-1796923 | 11/2017 | | |
| KR | 2018007266 A | * | 1/2018 | .......... A23L 33/105 |
| WO | WO 2012-157790 | 11/2012 | | |

OTHER PUBLICATIONS

Bodine et al. (2001) "Akt/mTOR pathway is a crucial regulator of skeletal muscle hypertrophy and can prevent muscle atrophy in vivo," Nature Cell Biology vol. 3, 1014-1019.
Foletta et al. (2011) "The role and regulation of MAFbx/atrogin-1 and MuRF1 in skeletal muscle atrophy," Pflugers Arch—Eur J Physiol 461, 325-335.
Lee et al. (2007) "The role of hormones, cytokines and heat shock proteins during age-related muscle loss," Clinical Nutrition 26, 524-534.
McKinnel et al. (2004) "Molecular Mechanisms of Muscle Atrophy," Cell, vol. 119, 907-910.
Nader (2005) "Molecular determinants of skeletal muscle mass: getting the "AKT" together," The International Journal of Biochemistry & Cell Biology 37, 1985-1996.
Choi et al. (2021) "Evaluation of Metabolite Profiles of Ginseng Berry Pomace Obtained after Different Pressure Treatments and Their Correlation with the Antioxidant Activity." Molecules 26, 284.
International Search Report dated Oct. 23, 2019, for corresponding International Application PCT/KR2019/008925 (filed Jul. 19, 2019) 7 pp.
Jowkar, et al. (2022) "Myasthenia Gravis" eMedicine Medscape, 45 pp.
Lee et al. (2018) "Black ginseng activates Akt signaling, thereby enhancing myoblast differentiation and myotube growth," Journal of Ginseng Research 42, 116-121 (available online Sep. 6, 2017).

\* cited by examiner

*Primary Examiner* — Qiuwen Mi
(74) *Attorney, Agent, or Firm* — Leydig, Voit & Mayer, Ltd.

(57) ABSTRACT

The present invention relates to a pharmaceutical composition for the prevention or treatment of muscle disease comprising a *Panax ginseng* berry extract as an active ingredient. The composition of the present invention alleviates the decrease in muscle weight and muscle fiber cross-sectional area caused by muscle atrophy, and reduces the increase in expression of MuRF-1 (Muscle RING-finger protein-1) and atrogin-1, which are involved in proteolysis of muscle proteins, so that it can be effectively used to prevent, ameliorate or treat muscle disease.

4 Claims, 2 Drawing Sheets

PHARMACEUTICAL COMPOSITION FOR PREVENTING OR TREATING MUSCLE DISEASES, CONTAINING GINSENG BERRY EXTRACT AS ACTIVE INGREDIENT

CROSS-REFERENCE TO RELATED APPLICATIONS

This application is a U.S. National Stage Application filed under 35 U.S.C. § 371 of International Application No. PCT/KR2019/008925, filed Jul. 19, 2019, which claims the benefit of Korean Application No. KR 10-2018-0096883, filed Aug. 20, 2018. Both of these applications are hereby incorporated by reference in their entireties.

BACKGROUND OF THE INVENTION

1. Field of the Invention

The present invention relates to a pharmaceutical composition for the prevention or treatment of muscle disease comprising a *Panax ginseng* berry extract as an active ingredient.

2. Description of the Related Art

Skeletal muscle is a tissue that accounts for 40 to 50% of a person's body weight, and one skeletal muscle is composed of a number of muscle fibers and connective tissues, has a horizontal pattern, and is involved in voluntary movement. Muscles play an important role in metabolic functions such as maintaining energy homeostasis and generating heat. The size of muscle is controlled by intracellular signaling pathways that induce anabolism or catabolism occurring within the muscle.

Muscle atrophy refers to a continuous decrease in muscle mass and is caused by muscle weakness and degeneration (McKinnell I W et al., Cell, 119(7): 907-910, 2004). Muscular atrophy is induced by decreased activity, oxidative stress, and chronic inflammation, which weakens muscle function and exercise capacity (Lee C E et al., Clinical Nutrition, 26(5): 524-534, 2007), and occurs when more proteolysis occurs than protein synthesis (Nader G A, The International Journal of Biochemistry and Cell Biology, 37(10): 1985-1996, 2005).

A representative factor involved in the synthesis of muscle proteins is mTOR (mammalian target of rapamycin). MTOR is an important factor that regulates the initiation of protein translation. The phosphorylated mTOR (p-mTOR) is an activated form, and its expression does not change significantly when the muscle is continuously immobilized, but when its activation increases, muscle atrophy is known to alleviate. MTOR increases muscle mass by inducing the synthesis of muscle proteins by activating 4EBP1 (4E-binding protein 1) and p70S6K (phosphorylated 70-kDa ribosomal S6 kinase), which initiate mRNA translation (Bodine et al., SC Nature cell biology, 3(11), 1014, 2001). On the other hand, the representative factors involved in the decomposition of muscle proteins include atrogin-1 and MuRF-1 (Muscle RING-finger protein-1), which are the muscle-specific E3 ubiquitin ligase factors. The expressions of atrogin-1 and MuRF-1 are significantly increased when the amount of activity is decreased (Foletta V C et al., PflugersArchiv-European Journal of Physiology, 461(3), 325-335, 2011), which promotes the proteosome-dependent proteolysis, resulting in decreased muscle mass. Therefore, promoting mTOR activity and inhibiting atrogin-1 and MuRF-1 expression increase the amount of muscle protein, thereby increasing muscle mass. Currently, as treatment methods for muscular atrophy, increasing mitochondrial production, muscle proteolysis inhibitors, and anti-inflammatory drugs have been suggested, but there is no clear treatment.

On the other hand, *Panax ginseng* is a plant belonging to the genus *Panax* of the family Araliaceae. It is a medicinal plant peculiar to Korea, native to the Korean Peninsula, and has been widely used since 2,000 years ago. Ginseng roots are mainly used for medicinal purposes. Ginseng growers harvest the seeds from 4-year-old ginseng to promote the growth of ginseng roots and secure the seeds when growing ginseng for 6 years. From 3-year-old, 5-year-old, and 6-year-old ginseng, the seeds are not harvested, but not only the flower stalks but also the stems are all removed, and thus about 3,000 tons of berries are discarded annually.

However, it has recently been reported that *Panax ginseng* berry contains a large amount of active ingredients, and exhibits various activities related to improvement of male sexual function (Korean Patent No. 10-1241050), prevention and treatment of Parkinson's disease/Alzheimer's disease (Korean Patent No. 10-1581497), treatment of type 2 diabetes (Korean Patent No. 10-1484502), etc., and therefore, it is being developed as a health functional food. However, there is no report on the activity of regulating muscle function of *Panax ginseng* berry so far.

SUMMARY OF THE INVENTION

It is an object of the present invention to provide a use of a *Panax ginseng* berry extract to prevent or treat muscle disease.

To achieve the above object, the present invention provides a pharmaceutical composition for the prevention or treatment of muscle disease comprising a *Panax ginseng* berry extract as an active ingredient.

The present invention also provides a health functional food for the prevention or amelioration of muscle disease comprising a *Panax ginseng* berry extract as an active ingredient.

The present invention also provides a cosmetic composition for the prevention or amelioration of muscle disease comprising a *Panax ginseng* berry extract as an active ingredient.

The present invention also provides a skin external preparation for the prevention or treatment of muscle disease comprising a *Panax ginseng* berry extract as an active ingredient.

The present invention also provides a feed additive or feed composition for the prevention or amelioration of muscle disease comprising a *Panax ginseng* berry extract as an active ingredient.

The present invention also provides a method for preventing or treating muscle disease comprising a step of administering a *Panax ginseng* berry extract to a subject.

In addition, the present invention provides a use of a *Panax ginseng* berry extract for use in the preparation of a medicament for the prevention or treatment of muscle disease.

Advantageous Effect

The *Panax ginseng* berry extract of the present invention alleviates the decrease in muscle weight and muscle fiber cross-sectional area caused by muscle atrophy, and reduces the increase in expression of MuRF-1 (Muscle RING-finger protein-1) and atrogin-1, which are involved in the decomposition of muscle proteins, so that it can be effectively used to prevent, ameliorate or treat muscle disease.

DESCRIPTION OF THE PREFERRED EMBODIMENTS

Figure 1:
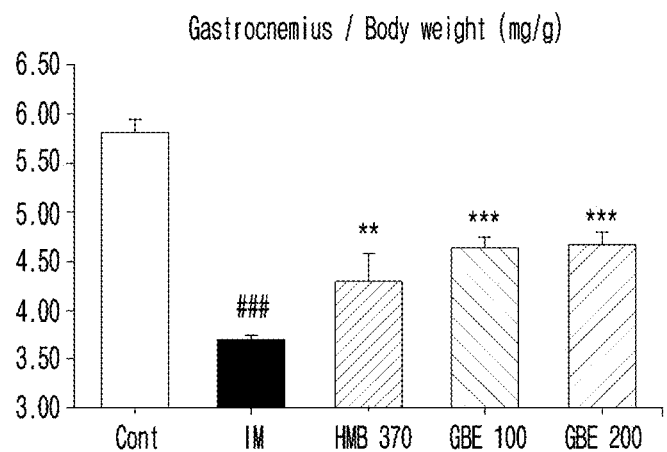
FIG. 1 is a diagram showing the muscle weight per unit body weight of the mouse gastrocnemius according to the administration of the *Panax ginseng* berry extract of the present invention (Cont: non-treated control; IM: the group induced with muscle atrophy; HMB 370: the group treated with 370 mg/kg of HMB (beta-hydroxy beta-methlybutyrate); GBM 100: the group treated with low dose (100 mg/kg) of the *Panax ginseng* berry extract; GBM 200: the group treated with high dose (200 mg/kg) of the *Panax ginseng* berry extract).

Hereinafter, the present invention is described in detail.

The present invention provides a pharmaceutical composition for the prevention or treatment of muscle disease comprising a *Panax ginseng* berry extract as an active ingredient.

The *Panax ginseng* berry extract can be prepared by a preparation method comprising the following steps:

1) preparing an extract by adding an extraction solvent to *Panax ginseng* berry;

2) filtering the extract of step 1); and 3) concentrating the filtered filtrate of step 2) under reduced pressure and drying thereof.

In the method above, the *Panax ginseng* berry of step 1) is either obtained by cultivation or purchased.

In the method above, the *Panax ginseng* berry can include the pericarps (everything except the seeds of the fruit) or seeds of the *Panax ginseng* berry, and specifically, can be the pericarps of the *Panax ginseng* berry.

In addition, the extraction solvent of step 1) can be water, alcohol, or a mixture thereof. The said alcohol is preferably $C_1$~$C_2$ lower alcohol. The lower alcohol herein is preferably ethanol or methanol. In one embodiment of the present invention, the extraction solvent can be water. The extraction solvent can be added in an amount of 1 to 10 mL per 1 g of the *Panax ginseng* berry used for extraction, and particularly, can be added in an amount of 1 to 5 mL.

The extraction method of step 1) can be shaking extraction, Soxhlet extraction, reflux extraction, ultrasonic extraction, or ultra-high pressure extraction. In one embodiment of the present invention, the extraction method can be ultra-high pressure extraction. At this time, the extraction temperature can be 15~45° C., preferably 15~35° C., and more preferably 20~30° C. In addition, the extraction pressure can be 200~1,000 MPa, preferably 300~900 MPa, and more preferably 400~800 MPa. The extraction time can be 10 seconds~1 hour, preferably 20 seconds~30 minutes, and more preferably 30 seconds~5 minutes. The extraction is preferably repeated 1~5 times, and more preferably repeated 1~3 times. In the range outside the conditions of the extraction temperature, the extraction pressure, the extraction time or the number of extraction, the extraction cannot be sufficiently performed, so the content of the active ingredient in the *Panax ginseng* berry extract may be reduced. Or, the extraction yield no longer increases, which may reduce the extraction efficiency.

The concentration under reduced pressure in step 3) is preferably performed by using a vacuum concentrator or a vacuum rotary evaporator. Drying is preferably performed by reduced-pressurized drying, vacuum drying, boiling drying, spray drying, or freeze drying.

The muscle disease refers to a disease caused by muscle wasting or degeneration, and can include any one or more selected from the group consisting of sarcopenia, atony, muscular atrophy, muscular dystrophy, muscle degeneration, myotonic dystrophy, amyotrophic lateral sclerosis, myasthenia and cachexia. The muscle wasting is characterized by a gradual loss of muscle mass and weakness and degeneration of voluntary muscles such as skeletal muscle or involuntary muscles such as cardiac muscle. The muscle wasting and degeneration are caused by genetic factors, acquired factors, and aging.

The composition of the present invention may be to alleviate the decrease in muscle weight and muscle fiber cross-sectional area due to muscle atrophy, and to alleviate the increase in expression of MuRF-1 or atrogin-1 protein, the factor involved in the proteolysis of muscle protein.

In a preferred embodiment of the present invention, the present inventors prepared a *Panax ginseng* berry extract, and then orally administered the *Panax ginseng* berry extract to the muscle atrophy induced mice. As a result, it was confirmed that the decrease in muscle weight and muscle fiber cross-sectional area was alleviated (see FIGS. 1 to 4), and the increase in expression of MuRF-1 or atrogin-1 protein involved in proteolysis of muscle protein was reduced (see FIG. 5). Therefore, the *Panax ginseng* berry extract can be effectively used in the prevention or treatment of muscle disease.

The pharmaceutical composition of the present invention preferably includes the *Panax ginseng* berry extract, the active ingredient, by 10~95 weight % for the total weight of the composition. The pharmaceutical composition of the present invention can include, in addition to the active ingredient, one or more effective ingredients having the same or similar function to the same.

The pharmaceutical composition of the present invention can include carriers, diluents, excipients or mixtures thereof generally used in biological preparations. The pharmaceutically acceptable carrier can be any carrier that is able to deliver the composition of the present invention in human body without limitation, which is exemplified by the compounds described in Merck Index, $13^{th}$ ed., Merck & Co. Inc., such as saline, sterilized water, Ringer's solution, dextrose solution, maltodextrin solution, glycerol, ethanol, or a mixture thereof. If necessary, a general additive such as antioxidant, buffer, and bacteriostatic agent can be additionally added.

When formulating the composition, diluents or excipients such as generally used fillers, extenders, binders, wetting agents, disintegrants, and surfactants can be added.

The composition of the present invention can be formulated as oral preparations or parenteral preparations. Oral formulations can include solid formulations and liquid formulations. The solid formulations for oral administration can be tablets, pills, powders, granules, capsules or troches. These solid formulations are prepared by mixing the composition with one or more suitable excipients such as starch, calcium carbonate, sucrose, lactose, gelatin, or a mixture thereof. Further, the solid preparation can contain lubricants such as magnesium stearate and talc. On the other hand, the liquid formulations can be suspensions, solutions, emulsions or syrups, and the above-mentioned formulations can contain various excipients such as wetting agents, sweeteners, aromatics and preservatives.

Formulations for parenteral administration can include injections, suppositories, powders for respiratory inhalation, aerosols for spray, powders and creams. The injection can include sterilized aqueous solutions, non-aqueous solvents, suspension solvents, emulsions, and the like. At this time, as the non-aqueous solvent or suspension solvent, propylene glycol, polyethylene glycol, vegetable oil like olive oil, injectable ester like ethylolate, and the like can be used.

The composition of the present invention can be administered by orally or parenterally and the parenteral administration includes intraperitoneal injection, intrarectal injection, subcutaneous injection, intravenous injection, intramuscular injection or intrathoracic injection.

The composition can be administered by the pharmaceutically effective amount. The effective amount can be determined according to the type of disease, the severity, the activity of the drug, the patient's sensitivity to the drug, the time of administration, the route of administration, the duration of treatment, the drugs being used simultaneously, and the like. However, for the desired effect, the amount of the active ingredient included in the pharmaceutical composition according to the present invention can be 0.0001~1 g/kg, specifically 0.001~500 mg/kg. The administration frequency is once a day or a few times a day.

The composition of the present invention can be administered alone or in combination with other therapeutic agents. In combination administration, the administration can be sequential or simultaneous.

The present invention also provides a health functional food for the prevention or amelioration of muscle disease comprising a *Panax ginseng* berry extract as an active ingredient.

The ginseng or *Panax ginseng* berry extract according to the present invention is as described above. In one embodiment of the present invention, the *Panax ginseng* berry can be the pericarps of *Panax ginseng* berry, and the extract can be extracted using water as a solvent, or can be extracted by ultra-high pressure treatment.

The muscle disease can include any one or more selected from the group consisting of sarcopenia, atony, muscular atrophy, muscular dystrophy, muscle degeneration, myotonic dystrophy, amyotrophic lateral sclerosis, myasthenia and cachexia.

The health functional food of the present invention may be to alleviate the decrease in muscle weight and muscle fiber cross-sectional area due to muscle atrophy, and to alleviate the increase in expression of MuRF-1 or atrogin-1 protein, the factor involved in the proteolysis of muscle protein.

In a preferred embodiment of the present invention, the present inventors prepared a *Panax ginseng* berry extract, and then orally administered the *Panax ginseng* berry extract to the muscle atrophy induced mice. As a result, it was confirmed that the decrease in muscle weight and muscle fiber cross-sectional area was alleviated (see FIGS. 1 to 4), and the increase in expression of MuRF-1 or atrogin-1 protein involved in proteolysis of muscle protein was reduced (see FIG. 5). Therefore, the *Panax ginseng* berry extract can be effectively used in the prevention or amelioration of muscle disease.

In this description, the "health functional food" indicates the food produced with the supplement of such nutrients that are often lack in daily diet or raw materials or components having a useful function for human body. The purpose of such a health functional food is to maintain a normal function of human body or to maintain health, and any general health food can be included.

The form and type of the health functional food are not particularly limited. Specifically, the health functional food can be in the form of tablets, capsules, powders, granules, liquids and pills. The health functional food can additionally include various flavors, sweetening agents or natural carbohydrates. The sweetening agents can be natural sweetening agents such as thaumatin and stevia extract, or synthetic sweetening agents such as saccharin and aspartame. The natural carbohydrates above can be monosaccharides, disaccharides, polysaccharides, oligosaccharides and glucose alcohols.

In addition to the ingredients mentioned above, the health functional food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, etc. All the mentioned ingredients can be added singly or together. The mixing ratio of those ingredients can be selected from 0.01 to 0.1 weight part per 100 weight part of the composition of the present invention.

The *Panax ginseng* berry extract of the present invention can be added as it is or as mixed with other food or food components. The content of active ingredients can be regulated according to the purpose of use. In general, the content in the health functional food can be 0.01 to 90 weight part of the total food weight. However, if long term administration is required for health and hygiene or regulating health condition, the content can be lower than the above but higher content can be accepted as well since arazyme has been proved to be very safe.

The present invention also provides a cosmetic composition for the prevention or amelioration of muscle disease comprising a *Panax ginseng* berry extract as an active ingredient.

The ginseng or *Panax ginseng* berry extract according to the present invention is as described above. In one embodiment of the present invention, the *Panax ginseng* berry can be the pericarps of *Panax ginseng* berry, and the extract can be extracted using water as a solvent, or can be extracted by ultra-high pressure treatment.

The muscle disease can include any one or more selected from the group consisting of sarcopenia, atony, muscular atrophy, muscular dystrophy, muscle degeneration, myotonic dystrophy, amyotrophic lateral sclerosis, myasthenia and cachexia.

The cosmetic composition of the present invention may be to alleviate the decrease in muscle weight and muscle fiber cross-sectional area due to muscle atrophy, and to alleviate the increase in expression of MuRF-1 or atrogin-1 protein, the factor involved in the proteolysis of muscle protein.

In a preferred embodiment of the present invention, the present inventors prepared a *Panax ginseng* berry extract, and then orally administered the *Panax ginseng* berry extract to the muscle atrophy induced mice. As a result, it was confirmed that the decrease in muscle weight and muscle fiber cross-sectional area was alleviated (see FIGS. 1 to 4), and the increase in expression of MuRF-1 or atrogin-1 protein involved in proteolysis of muscle protein was reduced (see FIG. 5). Therefore, the *Panax ginseng* berry extract can be effectively used in the prevention or amelioration of muscle disease.

The cosmetic composition of the present invention can include the *Panax ginseng* berry extract at the concentration of 0.1~50 weight %.

The cosmetic composition of the present invention can be formulated in any form that can be accepted in the art, which is exemplified by solution, suspension, emulsion, paste, gel, cream, lotion, powder, soap, surfactant-containing cleansing, oil, powdered foundation, emulsified foundation, wax foundation and spray, but not always limited thereto. Particularly, the cosmetic composition of the present invention can be prepared in the form of soft lotion, nutrition lotion, nutrition cream, massage cream, essence, eye cream, cleansing cream, cleansing foam, cleansing water, pack, spray or powder.

In the case that the cosmetic composition of the present invention is formulated as paste, cream or gel, the composition can include animal oil, vegetable oil, paraffin, starch, tracanth, cellulose derivative, polyethylene glycol, silicon, bentonite, silica, talk, zinc oxide, or a mixture thereof as a carrier. In the case that the cosmetic composition is formulated as powder or spray, the composition can include lactose, talc, silica, aluminum hydroxide, calcium silicate, polyamide powder, or a mixture thereof as a carrier. In particular if the composition of the present invention is formulated as spray, chlorofluorohydrocarbon, propane/butane or dimethyl ether can be additionally included.

In the case that the cosmetic composition of the present invention is formulated as liquid or emulsion, the composition can include solvent, solubilizer, emulsifier, or a mixture thereof as a carrier. The examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition of the present invention is formulated as suspension, the composition can include liquid diluent such as water, ethanol or propylene glycol; suspending agent such as ethoxylated isostearyl alcohol, polyoxyethylene sorbitol ester and polyoxyethylene sorbitan ester; microcrystalline cellulose; aluminum methahydroxide; bentonite; agar; and tragacanth; or a mixture thereof as a carrier.

In the case that the cosmetic composition of the present invention is formulated as surfactant-containing cleansing, the composition can include aliphatic alcohol sulfate, aliphatic alcohol ether sulfate, sulfosuccinic monoester, isethionate, imidazolinum derivative, methyltaurate, sarcosinate, fatty acid amide ether sulfate, alkyl amidobetain, aliphatic alcohol, fatty acid glyceride, fatty acid diethanolamide, vegetable oil, lanolin derivative, ethoxylated glycerol fatty acid ester, or a mixture thereof as a carrier.

In addition to the carrier component, the cosmetic composition of the present invention can include antioxidants, stabilizers, solubilizers, moisturizers, pigments, fragrances, sunblocks, color developing agents, surfactants, or mixtures thereof as additives. The additive can be used as long as it is a material commonly used in the preparation of a cosmetic composition.

The present invention also provides a skin external preparation for the prevention or treatment of muscle disease comprising a *Panax ginseng* berry extract as an active ingredient.

The ginseng or *Panax ginseng* berry extract according to the present invention is as described above. In one embodiment of the present invention, the *Panax ginseng* berry can be the pericarps of *Panax ginseng* berry, and the extract can be extracted using water as a solvent, or can be extracted by ultra-high pressure treatment.

The muscle disease can include any one or more selected from the group consisting of sarcopenia, atony, muscular atrophy, muscular dystrophy, muscle degeneration, myotonic dystrophy, amyotrophic lateral sclerosis, myasthenia and cachexia.

The skin external preparation of the present invention may be to alleviate the decrease in muscle weight and muscle fiber cross-sectional area due to muscle atrophy, and to alleviate the increase in expression of MuRF-1 or atrogin-1 protein, the factor involved in the proteolysis of muscle protein.

In a preferred embodiment of the present invention, the present inventors prepared a *Panax ginseng* berry extract, and then orally administered the *Panax ginseng* berry extract to the muscle atrophy induced mice. As a result, it was confirmed that the decrease in muscle weight and muscle fiber cross-sectional area was alleviated (see FIGS. 1 to 4), and the increase in expression of MuRF-1 or atrogin-1 protein involved in proteolysis of muscle protein was reduced (see FIG. 5). Therefore, the *Panax ginseng* berry extract can be effectively used in the prevention or amelioration of muscle disease.

The skin external preparation of the present invention can include pharmaceutically acceptable carriers and excipients. The carrier and excipient can include preservatives, stabilizers, hydrating agents, emulsifires and buffers. Specifically, the excipient can be lactose, dextrin, starch, mannitol, sorbitol, glucose, saccharose, microcrystalline cellulose, gelatin, polyvinylpyrrolidone, or a mixture thereof. The skin external preparation can be appropriately prepared according to the method well known in the art. The skin external preparation can be prepared in the form of powder, gel, ointment, cream, liquid, and aerosol.

The present invention also provides a feed additive or feed composition for the prevention or amelioration of muscle disease comprising a *Panax ginseng* berry extract as an active ingredient.

In this description, the "feed" refers to any natural or artificial diet, one meal, etc., or a component of the one meal, for animals to eat, ingest, and digest. The feed can be classified into various types according to nutritional value, main ingredient, distribution, moisture content, blending condition and processing type. The feed can be roughage, enriched feed, supplement feed, protein feed, starch feed, fat feed or fiber feed, but not always limited thereto.

In this description, the "feed additive" refers to a substance added to the feed for various effects such as supplementing nutrients and preventing weight loss, improving digestibility of fiber in the feed, improving milk quality, preventing reproductive disorders and improving fertility, and preventing high temperature stress in the summer. The feed additive of the present invention is supplement feed according to Control of Livestock and Fish Feed Act, and mineral preparations such as sodium hydrogen carbonate, bentonite, magnesium oxide and complex minerals, mineral preparations like trace minerals such as zinc, copper, cobalt and selenium, vitamins such as keratin, vitamin E, vitamins A, D and E, nicotinic acid and vitamin B complex, protective amino acids such as methionine and lysine, protected fatty acids such as fatty acid calcium salts, probiotics (lactic acid bacteria), yeast cultures, live bacteria such as fungal fermented products, yeast preparations, and the like can be additionally included.

The ginseng or *Panax ginseng* berry extract according to the present invention is as described above. In one embodiment of the present invention, the *Panax ginseng* berry can be the pericarps of *Panax ginseng* berry, and the extract can be extracted using water as a solvent, or can be extracted by ultra-high pressure treatment.

The muscle disease can include any one or more selected from the group consisting of sarcopenia, atony, muscular atrophy, muscular dystrophy, muscle degeneration, myotonic dystrophy, amyotrophic lateral sclerosis, myasthenia and cachexia.

The feed additive or feed composition of the present invention may be to alleviate the decrease in muscle weight and muscle fiber cross-sectional area due to muscle atrophy, and to alleviate the increase in expression of MuRF-1 or atrogin-1 protein, the factor involved in the proteolysis of muscle protein.

In a preferred embodiment of the present invention, the present inventors prepared a *Panax ginseng* berry extract, and then orally administered the *Panax ginseng* berry extract to the muscle atrophy induced mice. As a result, it was confirmed that the decrease in muscle weight and muscle fiber cross-sectional area was alleviated (see FIGS. 1 to 4), and the increase in expression of MuRF-1 or atrogin-1 protein involved in proteolysis of muscle protein was reduced (see FIG. 5). Therefore, the *Panax ginseng* berry extract can be effectively used in the prevention or amelioration of muscle disease.

Since the feed additive of the present invention has the effect of preventing or ameliorating muscle disease, it is possible to prevent muscle disease by continuously ingesting the feed additive to poultry, livestock, etc., and to improve muscle disease that has already occurred.

In addition, the feed additive can additionally include a carrier acceptable for poultry and livestock. Known carriers and stabilizers can be added to the feed additive, and various nutrients such as vitamins, amino acids, minerals, antioxidants, antibiotics, antibacterial agents and other additives can be added thereto as needed. The form of the feed additive can be powders, granules, pellets, suspensions, and the like.

In the case of supplying the feed additive, it may be supplied alone or mixed with feed for poultry and livestock.

The feed composition of the present invention has the effect of preventing or ameliorating muscle disease. Therefore, it is possible to prevent muscle disease by continuously ingesting the feed composition to poultry, livestock, etc., and to improve muscle disease that has already occurred.

In addition, the feed composition can be prepared by adding the *Panax ginseng* berry extract in an appropriate effective concentration range according to various feed manufacturing methods known in the art.

The subject to which the feed composition is applied is not particularly limited as long as it is a subject for the purpose of preventing or ameliorating muscle disease. The composition can be applied to any subject such as non-human animals like monkeys, dogs, cats, rabbits, marmottes, rats, mice, cows, sheep, pigs and goats, birds, or fishes.

The present invention also provides a method for preventing or treating muscle disease comprising a step of administering a *Panax ginseng* berry extract to a subject.

In one embodiment of the present invention, the *Panax ginseng* berry extract can be an extract of the *Panax ginseng* berry pericarps (everything except the seeds of the *Panax ginseng* berry).

The *Panax ginseng* berry extract or the *Panax ginseng* berry pericarp extract according to the present invention can have the characteristics as described above in this specification. On the other hand, the subject can be a mammal or non-mammal, for example, a human, and alternatively, the subject can be an individual suffering from muscle disease or an individual at risk of muscle disease.

The *Panax ginseng* berry extract of the present invention can be administered orally or parenterally and the parenteral administration includes external application, intraperitoneal injection, intrarectal injection, subcutaneous injection, intravenous injection, intramuscular injection or intrathoracic injection.

The *Panax ginseng* berry extract of the present invention can be administered by the pharmaceutically effective amount. The term "pharmaceutically effective amount" herein indicates the amount enough to treat a disease with applicable, reasonable or risky concentration. The effective amount can be determined according to the type of disease, the severity, the activity of the drug, the patient's sensitivity to the drug, the time of administration, the route of administration, the duration of treatment, the drugs being used simultaneously, and the like. The *Panax ginseng* berry extract of the present invention can be administered as an individual therapeutic agent or administered in combination with other therapeutic agents, sequentially or simultaneously, and can be administered single or multiple. It is important to administer an amount capable of obtaining the maximum effect in the minimum amount without side effects in consideration of all the above factors, and this can be easily determined by a person skilled in the art. A typical dosage unit for determining the therapeutically effective dose is calculated based on the amount of the active ingredient that can be administered to a human subject weighing 70 kg in a single dose. However, it is understood that the exact therapeutically effective dose of the active ingredient varies with the relative amount of each active ingredient used, the drug used and the rate of increase.

In addition, the present invention provides a use of a *Panax ginseng* berry extract for use in the preparation of a medicament for the prevention or treatment of muscle disease.

In one embodiment of the present invention, the *Panax ginseng* berry extract can be an extract of the *Panax ginseng* berry pericarps (everything except the seeds of the *Panax ginseng* berry).

Hereinafter, the present invention will be described in detail by the following examples.

However, the following examples are only for illustrating the present invention, and the contents of the present invention are not limited thereto.

Example 1: Preparation of *Panax ginseng* Berry Extract 100 kg of the *Panax ginseng* berry harvested from ginseng aged 4 years or older was washed, and the washed *Panax ginseng* berry was put in a seed separator with three times the amount of purified water and separated. As a result, the *Panax ginseng* berry pericarp (the rest excluding the seeds of the fruit) was obtained. After processing the obtained product containing the pericarps with a pressure of 600 MPa at room temperature (around 25° C.) for one minute, the *Panax ginseng* berry extract was obtained using a general press.

Experimental Example 1: Confirmation of Changes in Muscle Weight and Muscle Fiber Cross-Sectional Area According to Administration of *Panax ginseng* Berry Extract Whether the *Panax ginseng* berry extract improves the reduction in muscle weight and muscle fiber cross-sectional area caused by muscle atrophy was confirmed through animal experiments.

1-1. Confirmation of Relief of Muscle Weight Reduction

Whether the *Panax ginseng* berry extract alleviates the muscle weight reduction caused by muscle atrophy was confirmed by the following method.

First, 5-week-old male C57BL/6 mice were adapted to the animal laboratory environment for 7 days and then divided into 5 groups according to the experimental conditions. Particularly, the experimental groups were divided into the non-treated control group (normal group, Cont), the group induced with muscle atrophy (induction group, IM), the positive control group induced with muscle atrophy and treated with 370 mg/kg of HMB (beta-hydroxy beta-methlybutyrate) (HMB treated group, HMB 370), the group induced with muscle atrophy and treated with low dose (100 mg/kg) of the *Panax ginseng* berry extract of Example 1 (*Panax ginseng* berry extract treated group, GBE 100), and the group induced with muscle atrophy and treated with high dose (200 mg/kg) of the *Panax ginseng* berry extract of Example 1 (*Panax ginseng* berry extract treated group, GBE 200). Muscle atrophy was induced by immobilization in which a fixation device made of 1.5 mL microfuge tube, clip and velcro tape was applied to one hind leg of a mouse according to 'Disease models & mechanisms, 8(9), 1059-1069, 2015'. HMB and the *Panax ginseng* berry extract were dissolved in 0.5% carboxymethyl cellulose (CMC) and administered to the mouse orally once a day for 14 days from the day of the leg immobilization. After 14 days, the gastrocnemius and quadriceps of the hind leg were extracted, weighed, and standardized based on the body weight.

Figure 2:
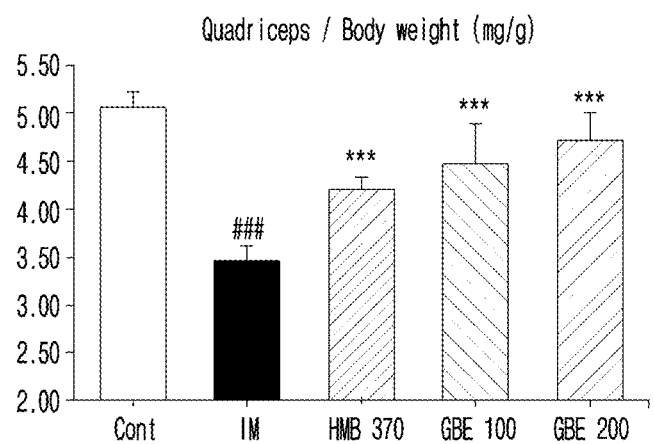
FIG. 2 is a diagram showing the muscle weight per unit body weight of the mouse quadriceps according to the administration of the *Panax ginseng* berry extract of the present invention (Cont: non-treated control; IM: the group induced with muscle atrophy; HMB 370: the group treated with 370 mg/kg of HMB (beta-hydroxy beta-methlybutyrate); GBM 100: the group treated with low dose (100 mg/kg) of the *Panax ginseng* berry extract; GBM 200: the group treated with high dose (200 mg/kg) of the *Panax ginseng* berry extract).

As a result, as shown in FIGS. 1 and 2, muscle atrophy was induced in the induction group (IM), and the weight of the gastrocnemius was reduced by about 40% and the weight of the quadriceps was reduced by about 33% compared to the normal group (Cont). In the positive control group treated with HMB, the weight of the gastrocnemius was reduced by about 24% and the weight of the quadriceps was reduced by about 17% compared to the normal group, indicating that HMB showed a protective ability of muscle atrophy of about 16%. In the group treated with low dose of the *Panax ginseng* berry extract (GBE 100), the weight of the gastrocnemius was reduced by about 20% and the weight of the quadriceps was reduced by about 11% compared to the normal group, indicating that the low dose treatment of the *Panax ginseng* berry extract showed about 16% and 21% of muscle atrophy protection, respectively. In the group treated with high dose of the *Panax ginseng* berry extract (GBE 200), the weight of the gastrocnemius was reduced by about 20% and the weight of the quadriceps was reduced by about 7% compared to the normal group, indicating that the high dose treatment of the *Panax ginseng* berry extract showed about 16% and 25% of muscle atrophy protection, respectively. From the above results, it was confirmed that the *Panax ginseng* berry extract alleviates the reduction in muscle weight caused by muscle atrophy and has a better protective effect on muscle atrophy per unit dose than HMB, the positive control.

1-2. Confirmation of Relief of Muscle Fiber Cross-Sectional Area Reduction

Whether the *Panax ginseng* berry extract alleviates the muscle fiber cross-sectional area reduction caused by muscle atrophy was confirmed by the following method. Particularly, the gastrocnemius tissue extracted in Experimental Example 1-1 was fixed with 4% paraformaldehyde, stained with hematoxylin and eosin (H&E), and the muscle fiber cross-sectional area was quantified using image J software.

Figure 3:
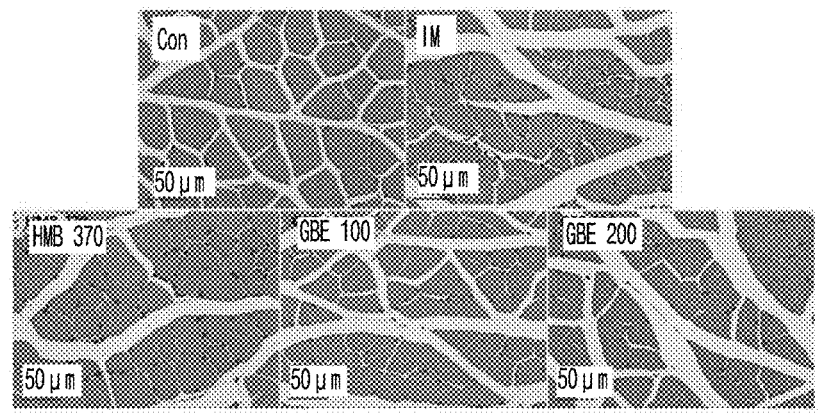
FIG. 3 is a diagram showing the size of the mouse muscle fiber according to the administration of the *Panax ginseng* berry extract (Cont: non-treated control; IM: the group induced with muscle atrophy; HMB 370: the group treated with 370 mg/kg of HMB (beta-hydroxy beta-methlybutyrate); GBM 100: the group treated with low dose (100 mg/kg) of the *Panax ginseng* berry extract; GBM 200: the group treated with high dose (200 mg/kg) of the *Panax ginseng* berry extract).
Figure 4:
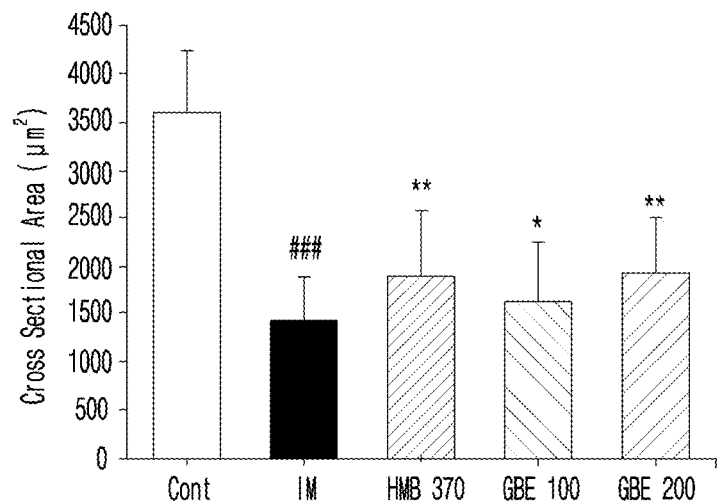
FIG. 4 is a diagram showing the quantified cross-sectional area of the mouse muscle fiber according to the administration of the *Panax ginseng* berry extract (Cont: non-treated control; IM: the group induced with muscle atrophy; HMB 370: the group treated with 370 mg/kg of HMB (beta-hydroxy beta-methlybutyrate); GBM 100: the group treated with low dose (100 mg/kg) of the *Panax ginseng* berry extract; GBM 200: the group treated with high dose (200 mg/kg) of the *Panax ginseng* berry extract).

As a result, as shown in FIG. 3, muscle atrophy was induced and the size of the gastrocnemius was significantly reduced in the induction group (IM) compared to the normal group (Cont). In the HMB treated group (HMB 370) and the groups treated with low dose and high dose of the *Panax ginseng* berry extract (GBE 100 and GBE 200), the reduction in muscle fiber size was alleviated. In addition, as shown in FIG. 4, the muscle fiber cross-sectional area was decreased by about 60% in the induction group, about 47% in the HMB treated group, about 55% in the group treated with low dose of the *Panax ginseng* berry extract, and about 46% in the group treated with high dose of the *Panax ginseng* berry extract, compared to the normal group, indicating that HMB and the *Panax ginseng* berry extract showed about 13%, 6% and 14% of muscle atrophy protection, respectively. From the above results, it was confirmed that the *Panax ginseng* berry extract alleviates the reduction in muscle fiber cross-sectional area caused by muscle atrophy and has a better protective effect on muscle atrophy per unit dose than HMB, the positive control.

Experimental Example 2: Confirmation of Changes in Proteolysis of Muscle Protein or Expression of Synthetic Factors According to Administration of *Panax ginseng* Berry Extract Whether the *Panax ginseng* berry extract alleviates the increase in expression of MuRF-1 (Muscle RING-finger protein-1) and atrogin-1 involved in proteolysis of muscle proteins was confirmed by Western blotting.

Particularly, protein was extracted from the gastrocnemius tissue extracted in Experimental Example 1-1 according to the manufacturer's protocol using a lysis buffer (17.115 g of sucrose, 2 mL of 1 M Tris buffer (Trizma base, pH 7.4), 0.2 mL of 0.5 M EDTA (pH 8.0), 4 protease inhibitor cocktail tablets, distilled water) containing cOmplete™ protease inhibitor cocktail tablets (Roche Diagnostics, USA). After confirming the protein concentration according to the manufacturer's protocol using Pierce™ BCA protein assay kit (Thermo Fisher Scientific, USA), and adjusting the concentration to a certain concentration, the same concentration of the protein was electrophoresed on 7.5% sodium dodecyl sulfate (SDS)-polyacrylamide gel and transferred to PVDF (polyvinylidene fluoride) membrane by electroblotting. The membrane was blocked with 5% skim milk at room temperature for 1 hour, and then incubated overnight with the primary antibody against MuRF-1 or atrogin-1 protein at 4° C. On the next day, the membrane was incubated with the secondary antibody for 2 hours, and then developed with LAS3000 luminescent image analyzer (Fujifilm Co., Japan). Anti-MuRF-1 antibody (Santa Cruz Biotechnology, USA), anti-atrogin-1 antibody (Santa Cruz Biotechnology, USA), and HRP (horseradish peroxidase)-conjugated secondary antibody (Santa Cruz Biotechnology, USA) were used as the antibodies.

Figure 5:
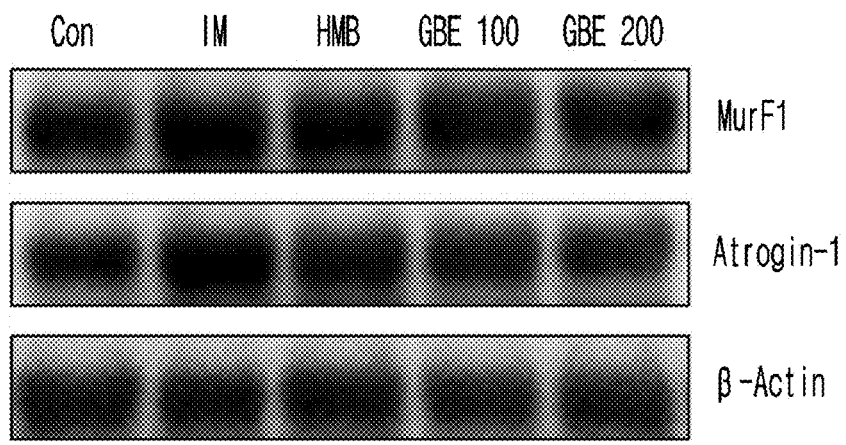
FIG. 5 is a diagram showing the expression of MuRF-1 or atrogin-1 protein in the mouse gastrocnemius administered with the *Panax ginseng* berry extract (Cont: non-treated control; IM: the group induced with muscle atrophy; HMB 370: the group treated with 370 mg/kg of HMB (beta-hydroxy beta-methlybutyrate); GBM 100: the group treated with low dose (100 mg/kg) of the *Panax ginseng* berry extract; GBM 200: the group treated with high dose (200 mg/kg) of the *Panax ginseng* berry extract).

As a result, as shown in FIG. 5, the expression of MuRF-1 and atrogin-1 proteins was significantly increased in the induction group (IM), compared to the normal group (Cont). The expression was decreased in the groups treated with the *Panax ginseng* berry extract (GBE 100 and GBE 200) dose-dependently. In the positive control group treated with HMB (HMB), the expression was similar to that in the group treated with low dose of the *Panax ginseng* berry extract. From the above results, it was confirmed that the *Panax ginseng* berry extract alleviates the increase in expression of MuRF-1 and atrogin-1 proteins caused by muscle atrophy dose-dependently and has a better protective effect on muscle atrophy than HMB, the positive control.

INDUSTRIAL APPLICABILITY

The *Panax ginseng* berry extract of the present invention alleviates the decrease in muscle weight and muscle fiber cross-sectional area caused by muscle atrophy, and reduces the increase in expression of MuRF-1 (Muscle RING-finger protein-1) and atrogin-1, which are involved in proteolysis of muscle proteins, so that it can be effectively used to prevent, ameliorate or treat muscle disease.

What is claimed is:

1. A method for treating sarcopenia, muscular atrophy, or muscle degeneration, comprising administering *Panax ginseng* berry extract in a pharmaceutically effective amount to a subject diagnosed with said sarcopenia, muscular atrophy, or muscle degeneration, wherein the *Panax ginseng* berry extract is generated using an extraction process comprising the steps of:
   1) adding an extraction solvent to *Panax ginseng* berry thereby forming an unfiltered extract;
   2) filtering the unfiltered extract of step 1) to obtain a filtrate; and
   3) concentrating the filtered filtrate of step 2) under reduced pressure and drying, thereby forming the *Panax ginseng* berry extract,
   wherein the extraction solvent comprises water, a $C_1$-$C_2$ lower alcohol, or combinations thereof, wherein step 1) further comprises extraction by ultra-high pressure treatment; and
   wherein the pharmaceutically effective amount comprises at least 100 mg of the *Panax ginseng* berry extract per kg of the subject.

2. The method for treating sarcopenia, muscular atrophy, or muscle degeneration according to claim 1, wherein the *Panax ginseng* berry is the pericarps of the *Panax ginseng* berry.

3. The method for treating sarcopenia, muscular atrophy, or muscle degeneration according to claim 1, wherein the extraction solvent comprises ethanol or methanol.

4. The method for treating sarcopenia, muscular atrophy, or muscle degeneration according to claim 1, wherein the composition alleviates increase in expression of MuRF-1 (Muscle RING-finger protein-1) or atrogin-1 protein.

* * * * *